United States Patent
Cruz et al.

(10) Patent No.: US 6,630,515 B2
(45) Date of Patent: *Oct. 7, 2003

(54) URINARY INCONTINENCE THERAPY

(75) Inventors: Francisco Cruz, Porto (PT); Helmer P. K. Agersborg, Blue Bell, PA (US)

(73) Assignee: Afferon Corporation, Wayne, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/138,448

(22) Filed: Aug. 21, 1998

(65) Prior Publication Data

US 2001/0006982 A1 Jul. 5, 2001

Related U.S. Application Data

(60) Provisional application No. 60/057,385, filed on Aug. 28, 1997.

(51) Int. Cl.[7] .......................... A61K 31/12; A61K 31/35
(52) U.S. Cl. ........................................ 514/691; 514/453
(58) Field of Search ................................. 514/691, 453

(56) References Cited

U.S. PATENT DOCUMENTS

| 4,939,149 A | 7/1990 | Blumberg | 514/691 |
| 5,021,450 A | 6/1991 | Blumberg | 514/453 |

OTHER PUBLICATIONS

Craft, R.M. and Porreca, F. "Temporal Parameters of Desensitization to Intravesical Resiniferatoxin in the Rat"; *Physiology & Behavior* (1994) 56(3):479–485.

Craft, R.M. and Porreca, F. "Tetracaine attenuates irritancy without attenuating desensitization produced by intravesical resiniferatoxin in the rat"; *Pain* (1994) 57:351–359.

Craft, R.M. et al. "Long-lasting desensitization of bladder afferents following intravesical resiniferatoxin and capsaicin in the rat"; *Pain* 61:317–323, 1993.

DeGroat, W.C. "A Neurologic Basis for the Overactive Bladder", *Urology* (1997) 50[Supplement 6A]:36–52.

Ishizuka, O. et al. "Urodynamic Effects of Intravesical Resiniferatoxin and Capsaicin in Conscious Rats With and Without Outflow Obstruction", *J. Urol.* (1995) 154:611–616.

Lazzeri, M. et al. "Urodynamic effects of intravesical resiniferatoxin in humans: preliminary results", *Urodinamica* (1996) 6:107–109.

Payne, C.K. "Epidemiology, pathophysiology, and evaluation of urinary incontinence and overactive bladder", *Urology* (1998) 51[Supplement 2A]:3–10.

*Primary Examiner*—Russell Travers
(74) *Attorney, Agent, or Firm*—Greenlee, Winner and Sullivan, P.C.

(57) ABSTRACT

The invention includes a method of treating neurogenic urinary dysfunction that comprises contacting urinary bladder mucosa of a patient afflicted with neurogenic urinary dysfunction with an effective dose of a homovanilloid compound, in particular a compound selected from the group RTX, TYX, 20-homovanillyl-mezerein or 20-homovanillyl-12-deoxyphorbol-13-phenylacetate. The invention includes treatment of urge incontinence due to detrusor hyperreflexia (DH). The invention also includes treatment of sensory hypersensitivity of the bladder resulting from prostate hypertrophy or interstial cystitis, as well as other neurogenic conditions resulting in increased micturition frequency or decreased bladder capacity, with or without frank incontinence.

13 Claims, No Drawings

URINARY INCONTINENCE THERAPY

CROSS REFERENCE TO RELATED APPLICATIONS

Priority is claimed from U.S. Provisional Application 60/057,385 filed Aug. 28, 1997.

STATEMENT RE. FEDERALLY SPONSORED RESEARCH AND DEVELOPMENT

Not applicable.

BACKGROUND OF THE INVENTION

Certain homovanilloid compounds, notably the homovanillyl diterpene esters resiniferatoxin (RTX) and tinyatoxin (TYX) are known to have physiological effects similar to capsaicin (CAP). Depending on which physiological response is measured, the homovanilloids are more potent than CAP, on a molar basis, by a factor of 10–10,000. In particular, RTX, TYX and other homovanilloids have been shown to be effective for desensitizing sensory nerves in a manner similar to CAP but at lower dosage (U.S. Pat. Nos. 4,939,149 and 5,021,450, incorporated herein by reference).

Urinary incontinence, the inability to maintain voluntary control of micturition, is a condition affecting millions of men and women. The control of micturition is a complex physiological process including neural reflex pathways, some with and some without central nervous system control, smooth and voluntary muscles and hormonal effects. (See review by DeGroat, [1997] Urology 50[Supplement 6A]:36–52.) A large subset of urinary incontinence is at least partly neurogenic. The clinical term "overactive bladder" is used generally to denote any form of incontinence characterized by increased frequency of micturition or desire to void, whether complete or episodic, and where loss of voluntary control ranges from partial to total. "Urge incontinence" is the involuntary loss of urine associated with an abrupt and powerful desire to void. Urge incontinence is usually, but not always, associated with the urodynamic finding of involuntary (uninhibited) contractions of the detrusor muscle. The detrusor muscle provides the primary force in expelling urine from the bladder. A large subset of patients with uninhibited detrusor have some sort of neurologic impairment, in which case the clinical term is "detrusor hyperreflexia" (DH). The term detrusor instability"or "unstable detrusor" is reserved for conditions where there is no neurologic abnormality. There is evidence suggesting that detrusor instability may result from subclinical neurologic disease or from primary muscle disease (Payne, C. K. [1998] Urology 51[Suppl.2A]:3–10). Common neurologic disorders associated with detrusor hyperreflexia (DH) are Parkinson's disease, stroke, diabetes, multiple sclerosis (MS), peripheral neuropathy and spinal cord injury.

Other types of urinary incontinence result from hypersensitivity of sensory (afferent) neurons of the urinary bladder. The desire to void and the reflexes resulting in micturition are initiated by (afferent) inputs from the urinary bladder including C-fiber transmitted afferent impulses. Certain inflammatory conditions, hormonal imbalance, prostate hypertrophy and the like can cause afferent hypersensitivity of the neurons of the bladder, resulting in increased frequency, unexpected urgency, and the like, leading to incontinence episodes of varying severity. Both DH and sensory hypersensitivity are included in the term "neurogenic urinary dysfunction" herein.

CAP has been used to treat patients with detrusor hyperreflexia (DH), by intravesical instillation. However, CAP is not suitable for routine usage in incontinence because there is intense burning and pain in the lower abdomen upon instillation, and there is a period of 2–4 days after treatment when symptoms actually deteriorate before any improvement is noted.

RTX has been tested in rats to assess possible efficacy in humans. Buck et al. (1990) International patent publication WO 90/14083, described studies designed to assess desensitizing effects of administering RTX into rat urinary bladders. The animals were anesthetized prior to perfusing the bladders with RTX. An immediate excitatory stage was observed upon initial perfusion, followed by decreasing excitation upon subsequent perfusions, indicating that desensitization was occurring. The use of local anesthetics to alleviate pain during RTX administration was discussed.

Ishizuka et al. (1995) J. Urol. 154:611–616 described studies demonstrating RTX-induced desensitization of vanilloid receptor-mediated release of tachykinins in the rat urinary bladder. Differences between the physiologic effects of RTX and CAP were noted. Desensitization to repeated doses of RTX was observed, but not to repeated doses of CAP. CAP was effective in reducing symptoms in rats having an experimentally induced hypertrophy, whereas RTX was not. RTX was stated to be 1000 times more potent than CAP.

Craft et al. (1994a) Physiol and Behavior 56:479–485 reported studies indicating pain induced by intravesical administration of RTX to rats. Both excitatory and desensitizing effects of CAP and RTX were attenuated by ruthenian red, a known cation channel blocker.

Craft et al. (1994b) Pain 57:351–359 reported tests to demonstrate that local anesthetics could reduce pain associated with administering RTX intravesicularly to rats.

Craft et al. (1995) Pain 61:317–323 described studies showing long-lasting desensitization of bladder afferents in rats treated with intravesicular CAP (10–100 $\mu$mol) or RTX (10–100 $\mu$mol).

Lazzeri et al. (1996) Urodinamica 6:107–109 reported studies on intravesicular administration of $10^{-8}$M (0.01 $\mu$M) RTX to normal human volunteers and patients with unstable detrusor. Normal patients reported no warn or burning sensation upon administration, and no changes in bladder function. Three of five patients having unstable detrusor reported an increased volume required to elicit first desire to void, while two patients had no significant urodynamic results. At the RTX concentration employed, the human subjects experienced no micturition reflex or burning upon administration, in contrast to reports in rats.

SUMMARY OF THE INVENTION

The invention is based on experimental evidence of effective therapy of humans experiencing neurogenic urinary dysfunction, including urge and mixed urge incontinence. The therapy includes intravesicular instillation of certain homovanilloid compounds, including resiniferatoxin (RTX), tinyatoxin (TYX), 20-homovanillyl-mezerein and 20-homovanillyl-12-deoxyphorbol-13-phenylacetate. Patients who benefit from the therapy include those with impairment of the micturition reflex, in particular those whose impairment involves the afferent branch of the reflex and those with hypersensitivity of bladder afferent nerves or C-fiber-transmitted sensory impulses. The therapy is effective for patients who have spinal cord damage, either due to trauma or related to disease, including, without limitation, inflammatory, auto-immune, vascular, metabolic, prostate hypertrophy, interstial systitis, genetic disease and infectious disease. The therapy is especially effective for patients whose incontinence is due to multiple sclerosis.

In general, treatment is conducted by administering RTX (or a functionally equivalent analog such as TYX) topically to the urinary bladder mucosa, by intravesicular instillation. A solution of a therapeutically effective amount of the compound (e.g. RTX) is retained in the bladder for a convenient time interval, e.g. about one hour, then excreted. A single such treatment can be effective for an extended period, such that a patient can be maintained by treatments once every 1–6 months. A major unexpected advantage of the use of RTX or its analog is that when administered at effective dosage the compounds do not cause pain or burning sensations, such as are associated with CAP treatment. Furthermore, patients experience no initial deterioration of their symptoms as is the case with CAP treatment. The therapy is therefore more tolerable and longer-lasting, compared to CAP treatment.

DETAILED DESCRIPTION OF THE INVENTION

Effective therapy for neurogenic urinary dysfunction can be palliative, symptomatic relief, since at present many of the underlying causes, e.g., spinal cord injury, MS, cannot be treated. A useful treatment is judged on practical clinical measurements of voluntary and involuntary urination including such things as patient diaries of frequency and incontinence episodes, frequency of catheterization, number of pads used, weighing pads to assess involuntary urine loss, arbitrary assessment of leakage severity, patient and physician assessment of patient's bladder control. Meaningful outcomes to the patient include reduced frequency, reduction of incontinent episodes and control of bladder functions. Physicians also conduct urodynamic measurements which can provide evidence of improvement and also give valuable information on a patient's bladder function. There are several ways of performing urodynamic measurements but all involve instilling either a gas or liquid into an empty bladder and observing pressure with volume changes. The following are some of the parameters which are typically measured:

Bladder Capacity: The capacity of a bladder with DH or DI may be reduced because involuntary contractions forcibly eliminate urine before substantial filling occurs. This causes problems not only in urinary frequency but also increases the frequency of required self-catheterization to empty the bladder. If bladder capacity is increased, the frequency of urination or self catheterization can be reduced and the patient should become more continent with less leakage and pad use.

Pressure at First Desire to Void: is associated with increased bladder capacity. An increase in value gives the patient greater confidence in social situations and provides a very meaningful contribution to quality of life.

Volume When Uninhibited Detrusor Contractions Occur: reflects the fact that more urine is allowed to accumulate before uninhibited contractions begin. In patients with an unstable bladder uninhibited detrusor contractions would, by reflex, follow the first desire to void. Some physicians diagnose urge incontinence based on uninhibited detrusor contractions.

Sphincter Abnormalities: One of the many problems associated with detrusor hyperreflexia is detrusor sphincter syssynergia (closure of the bladder sphincter). This increased tonicity may control some involuntary urine loss but it also may cause a reflux of urine back into the kidney and cause hydronephrosis, as an undesirable clinical accompaniment of incontinence.

Finally, many urge incontinence patients use anticholinergic drugs. Effective therapy can be assessed by monitoring the level of drug use. Lower use indicates improved continence. Since these drugs have serious side-effects, this is important to the patient.

Clinical studies reported herein include the following: observations from the patient's urination diary and their overall assessment of bladder function, maximum cystometric capacity of the bladder, and daily urinary frequency and incontinence episodes. In addition, side-effects, if any, were carefully assessed, notably burning and irritation. Useful and effective treatment is that which alleviates any of the symptoms associated with neurogenic urinary dysfunction.

Patients chosen for study were of either sex, between the ages of 30 and 75, and weighing between 60 kg and 110 kg. Patients were selected having bladder hyperactivity associated with spinal cord injury, multiple sclerosis, peripheral neuropathy, muscular dystrophy or bladder instability. Pregnant women were excluded from the study as were those exposed to any other investigational drug within 30 days of baseline, those exposed to drugs affecting bladder performance or detrusor function within 10 days of baseline, those with known chemical addiction, those with seizure activity or major psychiatric disorders, and those with clinically significant cardiovascular, renal or hepatic disease, upper respiratory disease, malignant disease or clinically significant abnormal clinical laboratory values. Patients taking anti-cholinergic drugs were generally excluded except in a rare instance at the discretion of the investigator, in which case the dosage of anti-cholinergic drug was not changed during the study. Patients previously treated with capsaicin were first monitored to insure a return to baseline parameters in the absence of capsaicin. Preliminary studies to determine RTX dosage efficacy were performed with patients who had previous experience with intravesical capsaicin administration for treatment of bladder hyperactivity. Once a dose range for the study was determined, both previously capsaicin-treated and -untreated patients were employed.

The molecular weight of RTX is 628.72 for the clinical studies described herein. A 10 $\mu$M stock solution, 6.3 $\mu$g/mL was prepared by dissolving 6.32 mg of 99.5% pure RTX in 1000 mL absolute ethanol. Solutions for therapeutic use were diluted from the ethanolic stock solution into sterile normal saline (0.9% w/v NaCl) or a saline-ethanol mixture such that the final solution was 10% (v/v) ethanol. Therapeutic efficacy was tested for RTX concentrations of 1 $\mu$M, 0.1 $\mu$M and 0.05 $\mu$M. The solutions were stable under refrigeration (4° C.) shielded from light. Prior to administration, RTX solutions were sterilized by filtration.

Bladder Measurements:

Fill cystometry: A two-way 8 F urethral catheter was inserted in the bladder under clean conditions. The residual urine was emptied. Infusion of saline at body temperature was started at a constant speed of 50 ml/s. Patients were asked to indicate the moment of first desire to void (FDV) and any other sensation. The infusion was stopped at compulsive desire to void and the infused volume taken as the maximal cystometric capacity (MCC). Bladder pressure at which MCC occurs was also recorded. A prophylactic antibiotic (ciprofloxacin, 500 mg every 8 hours) was given during the next 48 hours.

Ice-Water test: The patient was clean catheterized with a two-way urethral catheter. A volume of 50 ml of iced saline (or half of the MCC found in cystometry) was put in a catheter-irrigating syringe and injected into the bladder during a period of 20 seconds. Bladder pressure was constantly measured. The test was considered positive (abnormal) if an involuntary bladder contraction was recorded during the next 60 seconds. If the first iced saline instillation does not evoke any contraction, the test was repeated another time before being considered negative (normal).

RTX Instillation: An 18 or 20 F three-way Foley catheter was used. The balloon was inflated to 20 ml and maintained gently pulled against the bladder neck to reduce leakage of RTX.

Up to 100 mL RTX solution was introduced into an emptied bladder, retained in the bladder for 30 minutes, then the bladder was emptied and rinsed with normal saline. Prior to treatment, baseline measurements of MCC, micturition frequency and ice water test response made. Following a single instillation of RTX, patients were tested again at 14, 20, 60 and 90 days.

The following patients were treated according to the above-described protocol:

1: Extradural abscess, walkers. Frequency and urgency.
2: MS, wheel chair. Frequency and urgency.
3: Spinal cord injury; walkers. Frequency and urgency.
4: MS, bed-ridden. Incontinence (pads permanently).
5: Transverse myelitis; walkers. Incontinence between maneuvers.
6: Vascular disease, walks with difficulty. Frequency, incontinence and urgency.
7: Iatrogenic (neurosurgery), wheel chair. Incontinence between maneuvers.
8: Spinal cord injury, walkers. Incontinence between maneuvers. Oxybutinin.
9: MS, walks with difficulty. Frequency, incontinence and urgency.
10: Spinal cord injury, paraplegic, automatic micturition, incontinent between ill maneuvers.
11: Spinal cord injury; paraplegic, self-catheterization, incontinent between catheterizations.
12: MS; walks with difficulty, urgency, frequency and incontinence.
13: Iatrogenic (neurosurgery); paraplegic, urgency, frequency and incontinence.
14: Iatrogenic (neurosurgery); walks using walker, urgency, frequency and incontinence.

Patients 1, 2, 6, 7, 8 and 13 received 0.05 $\mu$M RTX. The rest received 0.1 $\mu$M RTX.

Patients 11 and 12 were originally treated with a placebo instillation of solvent lacking RTX. Both patients were monitored for one month but experienced no improvement in objective or subjective measurement. Subsequently both patients were treated with 0.1 $\mu$M RTX.

For patients able to do spontaneous micturitions (#1, 2, 3, 4, 6, 9, 12 and 13), all but two (patient #4), a bed-ridden individual who required permanent use of pads, micturating directly into them) and patient # 14, had decreased frequency after RTX treatment, lasting up to 60 days post-treatment. Of the patients who were entirely incontinent, (#3, 4, 6, 9, 12, 13 and 14) five (#3, 6 and 9, 12 and 13) achieved full continence after RTX instillation. All patients in the group but one (#1) showed clear improvement (increase) in MCC, although even in case #1, an increase over baseline was observed at 6 months post-treatment.

For patients requiring self-catheterization or supra-pubic maneuvers (#4, 5, 7, 8 and 11), all but one (#4) reported improvement after RTX administration. Case #8, although not showing any modification of MCC, reported urine losses occurring later between catheterizations and in smaller amounts. Case #7 had improved MCC and reported only one incontinence episode between days 14 and 30 post-treatment, compared to at least once between catheterizations prior to RTX treatment. Case #11 showed no improvement during administration of placebo. After RTX (0.1 $\mu$M) the patient reported substantially decreased incontinence episodes, from 0 to 1–3, although frequency and MCC values were not improved.

Patient #10, wheel-chair bound with spinal cord injury, was treated with 100 $\mu$M RTX instillation. Prior to treatment, this patient required intermittent catheterization, or micturition triggered by suprapubic maneuver four times per day with incontinence episodes more than 7 times per day. Baseline MCC was only 80 ml. MCC measured at day 14 increased to 500 ml. Continence improved substantially, with many days totally dry and leaks on the worst day no more than 2–3 times per day. Furthermore, the losses during incontinent episodes were much smaller.

For all patients, itching or mild discomfort were the only symptoms evoked by RTX, noted only by a few patients during the first minutes of the treatment. Vital signs did not change and no patients showed evidence of being under intense pain. There was no evidence of severe irritation or transient hyperirritability as seen with CAP.

In the foregoing 14-patient study, meaningful effects, decreases in frequency, urge or wetness were seen in 71% of patients. Two of the four non-responders had not responded to CAP. Tables 1–4 summarize the pooled data. In Table 1, bladder capacity (MCC) increased in 11 out of the 14 patients. In patients were the MCC was initially low (less than 100 ml) an increase was observed, but the effect was less for patients with higher initial capacity.

TABLE 1

Efficacy Analysis: Bladder Capacity <200 mL; n-7

| Days | Bladder Capacity (mLs) | Change from Pre-RTX | % Change |
|---|---|---|---|
| Pre-RTX | 86 | — | — |
| 14 | 279 | +193 | +224 |
| 30 | 220 | +134 | +156 |
| 60 | 223 | +137 | +159 |
| 90 | 277 | +191 | |

In Table 2, overall assessment of frequency after RTX treatment summarized for the sevet patients whose baseline frequency was greater than 1-micturition/day. For patients whose baseline frequency was low, little change was noted after RTX administration. For patients using pads or sheaths, frequency was not assessable.

TABLE 2

Efficacy analysis: Frequency ≧10/day; n = 7

| Days | Mean Frequency/day | Change from Pre-RTX | % Change |
|---|---|---|---|
| Pre-RTX | 15.7 | — | — |
| 14 | 10.4 | −5.3 | −34 |
| 30 | 11.3 | −4.4 | −28 |

TABLE 2-continued

Efficacy analysis: Frequency ≧10/day; n = 7

| Days | Mean Frequency/day | Change from Pre-RTX | % Change |
|---|---|---|---|
| 60 | 10.4 | −5.3 | −34 |
| 90 | 10.8 | −4.9 | −31 |

In Table 3, the combined data number of incontinent episodes per day is summarized for eight patients having more than one incontinent episode/day. Certain patients had symptoms of frequency and/or urgency but no incontinence, while others could not be assessed due to pad or urosheath use. Of the eight evaluable patients only one did not show a positive benefit from RTX therapy.

TABLE 3

Efficacy analysis: Incontinence >episode/day; n = 8

| Days | Mean Incontinent Episodes/day | Difference from Pre-RTX | % Change |
|---|---|---|---|
| Pre-RTX | 3.6 | — | — |
| 14 | 2.0 | −1.6 | −44 |
| 30 | 1.3 | −2.3 | −64 |
| 60 | 1.2 | −2.4 | −67 |
| 90 | 1.5 | −2.1 | −58 |

Table 4 summarizes the data from all 14 patients, comparing baseline, pre-RTX values with those observed after treatment up to 90 days.

TABLE 4

Efficacy analysis: Comparison of selected major efficacy parameters; intent-to-treat analysis; n = 14

| Days | Mean Frequency/day | Difference from pre-RTX | Mean incontinent episodes | Difference from pre-RTX | Mean bladder capacity (mL) | Difference from pre-RTX |
|---|---|---|---|---|---|---|
| Pre-RTX | 9.1 | — | 2.1 | — | 182 | — |
| 14 | 6.9 | −2.2 | 1.0 | −1.0 | 277 | 95 |
| 30 | 7.5 | −1.6 | 0.7 | −1.4 | 247 | 64 |
| 60 | 7.0 | −2.1 | 0.4 | −1.7 | 228 | 45 |
| 90 | 6.2 | −2.6 | 0.6 | −1.5 | 330 | 148 |

A separate study was undertaken with administration of 0.1 μM RTX to a group of 6 patients with MS. One of the six had a relapse of MS between RTX administration and urodynamic measurement, making results difficult to evaluate. One patient was bedridden with an indwelling catheter. Despite the catheter, occasional bursts of detrusor hyperreflexia caused explosive expulsions of urine such that urine leaked around the catheter. No urinary dynamic measurements were taken but 100 ml of 1 μM solution was administered. There was no urge and no leakage since (six weeks). The remaining four patients were all on crutches or in wheelchairs. They were on scheduled intermittent self-catheterizations and remained so. Table 5 shows the changes one month after treatment.

TABLE 5

| Patient # | Dose nM | Kurtzke Score | LVB | LVA | DB | DA | CAPB | CAPA | ULPB | ULPA |
|---|---|---|---|---|---|---|---|---|---|---|
| Patient 6 | 500 | 6 | 60 | 10 | 2 | 01 | 200 | 360 | 96 | 40 |
| Patient 7 | 500 | 6 | 100 | 80* | 2 | 1 | 180 | 750 | 63 | 36 |
| Patient 9 | 1000 | 6 | 180 | 0 | 2 | 2 | 100 | 300 | 32 | 30 |
| Patient 10 | 1000 | 6 | 180 | 0 | 2 | 2 | 280 | 460 | 46 | 44 |

*Stress incontinence
LVB Loss volume before RTX
LVA Lost volume after RTX
DB Drug before RTX
DA Drug after RTX
CAPB Capacity before RTX
CAPA Capacity after RTX
ULPB Urine loss pressure before RTX
ULPA Urine loss pressure after RTX Urinary loss decreased after instillation of RTX in all four patients. The one patient with little change was found to have stress incontinence and was given a subsequent collagen injection to good effect. Capacity was increased in all patients and urine loss pressure was decreased in all four although minimally in two. All of the patients treated considered the treatment worthwhile. No side effects, particularly no meaningful burning or irritation were observed, even at doses of 1.0 µM RTX.

The foregoing results establish the efficacy of RTX and related homovanillyl diterpene esters or TYX for topical treatment or urinary incontinence by urinary bladder instillation. Effective doses range from 0.05 µM-2.0 µM RTX. At higher doses there is increasing risk of bladder areflexia. In addition, higher concentrations of RTX can require a larger solvent concentration to maintain the RTX in solution, which in turn increases the potential for causing irritation of the bladder mucosa due to solvent. A single instillation is effective for up to 6 months. Patients afflicted with urge incontinence vary widely due to the variety of conditions that can cause the problem and the severity of the affliction. Therefore, it will be understood by those skilled in the art that the dosage and frequency of treatment will be customized to the patients' needs, based on clinical evaluations of the treatment. The treatment has been found to be especially effective for patients afflicted with multiple sclerosis. Administration is topical, by contacting the urinary bladder mucosa with RTX (or TYX or other analog). Any means by which an effective concentration of RTX can be brought into contact with the bladder mucosa can be employed. A contact time of from ½–2 hours is sufficient for effective therapy.

RTX and other homovanilloids are insufficiently soluble in water to permit delivering a therapeutic dose in completely aqueous medium. However, the compounds are soluble in ethanol. Pure ethanol cannot be instilled into the bladder because it causes severe pain and irritation of the bladder mucosa. However, it has been found that ethanolic solutions of RTX can be diluted into an aqueous medium such as normal saline, such that RTX remains in solution and the ethanol content is sufficiently low (not greater than 20% (v/v) ethanol) to avoid significant irritation. RTX can be stably maintained as a stock solution in absolute ethanol, stored in the dark, preferably refrigerated. The stock solution can be diluted into an aqueous medium, such as physiological saline, or into an ethanol-saline mix, such that the final ethanol concentration is at least 10% (v/v), when prepared as described, RTX remains in solution. The foregoing solution, after filter sterilization, can be directly instilled into the urinary bladder. A typical instillation volume is 100 ml, although it is possible to instill somewhat larger or smaller volumes, as is understood in the art.

The other primary solvents of homovanilloids can be employed instead of, or in combination with, ethanol and one another, as is known in the art, provided they are not toxic or irritating to bladder mucosa in the amounts used. Such solvents include, for example, dimethyl sulfoxide, lower primary and secondary alcohols having 2–5 carbons, and other semi-polar hydrocarbons as is known in the art. Co-solvents, to enhance solubility in water-alcohol mixtures include propylene glycol, glycerol, polyethylene glycol, as well as medium chain triglycerides, ethyl oleate and the like. Although the use of surfactant, such as non-ionic detergents, e.g. polysorbate 80, can enhance dispersion and help prevent precipitation, it is preferred to avoid concentrations of greater than 1.0% (w/v) due to deleterious effects on bladder mucosa at higher concentrations. Aqueous solutions can be buffered, using physiologically acceptable buffers, to maintain solution at a desired pH, preferably within the pH range of normal urine. Formulations of homovanilloids can optionally include stabilizers, such as citric acid, ascorbic acid, cyclodextrin, EDTA, BHT and NF, as known in the art.

Homovanilloid formulations can also be provided as lyophilized powders. Solutions of RTX or other homovanilloids can include bulking agents such as sodium chloride, mannitol, polyvinylpyrrolidone and the like, to provide sufficient matter for ease of handling after lyophilization.

The final composition to be instilled into the bladder preferably contains sufficient solvent to maintain active ingredients in solution while at the same time sufficiently compatible with bladder mucosa that instillation does not result in pain, irritation or toxicity 1–5 to bladder mucosa.

Since the effects of homovanilloid treatment are long-lasting, it will be especially convenient to provide the therapeutic compound, e.g., RTX, prepackaged for single dose administration. Accordingly, a kit is provided, having a unit dose of RTX or other homovanilloid present in a storage-stable form, dissolvable or dilutable to the desired instillation volume, e.g., 100 ml, together with appropriate packaging and handling devices for convenience of mixing and to maintain sterility prior to instillation. Such a kit can include, for example, a first container containing active ingredient in a stable storage form, either as a unit dose in a stock solution or a unit dose as lyophilized powder; and a second container containing diluent, or solvent and diluent, either separate or combined, the volume of which will provide a unit dose of therapeutic compound in a volume sufficient for a single intravesicular instillation; means for combining diluent with the stock solution or lyophilized powder; and optionally, means for transferring the instillation dose to the patient. Means for transferring diluent to the stock solution or lyophilized powder can include, but are not limited to, syringes or multi-chambered containers having a breachable internal seal separating active ingredient from diluent. Means for transferring the instillation dose to the patient can include, but are not limited to, sterile tubing and appropriate fittings for connecting the tubing to a patient's catheter.

The invention therefore includes a method of treating neurogenic urinary dysfunction that comprises contacting urinary bladder mucosa of a patient afflicted with neurogenic urinary dysfunction with an effective dose of a homovanilloid compound, in particular a compound selected from the group RTX, TYX, 20-homovanillyl-mezerein or 20-homovanillyl-12-deoxyphorbol-13-phenylacetate. The invention includes treatment of urge incontinence due to detrusor hyperreflexia (DH). The invention also includes treatment of sensory hypersensitivity of the bladder resulting from prostate hypertrophy or interstial cystitis, as well as other neurogenic conditions resulting in increased micturition frequency or decreased bladder capacity, with or without frank incontinence.

The invention is effective for treatment of urinary incontinence experienced by a patient afflicted with multiple sclerosis.

The invention also includes a composition comprising a homovanilloid compound, for example RTX, and a physiologically acceptable diluent suitable for urinary bladder instillation.

The invention further comprises a treatment kit for treating neurogenic urinary dysfunction, comprising a homovanilloid compound, such as RTX, in unit dosage form, a physiologically acceptable diluent, and sterile, disposable apparatus for urinary bladder instillation.

Although the invention has been disclosed by examples of specific embodiments, other embodiments, methods, compositions, active ingredients, indications, compositions and kits will be apparent to those skilled in the art. All such alterations and extensions are included with the invention as disclosed and claimed herein.

What is claimed is:

1. A method for alleviating symptoms of neurogenic urinary dysfunction comprising administering by intravesicular instillation to a human patient having said symptoms a therapeutically effective concentration in the range from 0.05 $\mu$M to 2.0 $\mu$M of a compound selected from the group resiniferatoxin, tinyatoxin, 20-homovanillyl-mezerein or 20-homovanillyl-12-deoxyphorbol-13-phenylacetate in a physiologically compatible solvent, said concentration being a concentration that does not cause meaningful burning or irritation to said patient.

2. The method of claim 1 wherein the symptoms of neurogenic urinary dysfunction are characterized as detrusor hyperreflexia.

3. The method of claim 2 wherein the detrusor hyperreflexia is associated with multiple sclerosis.

4. The method of claim 2 wherein the detrusor hyperreflexia is associated with spinal cord injury.

5. The method of claim 1 wherein the symptoms of neurogenic urinary dysfunction are characterized by hypersensitivity of bladder afferent nerves.

6. The method of claim 5 wherein the hypersensitivity is associated with prostate hypertrophy.

7. The method of claim 1 wherein the effective concentration lies in the range from 0.05 $\mu$M to 1.0 $\mu$M.

8. The method of claim 1 wherein the compound is resiniferatoxin.

9. The method of claim 1 wherein the physiologically compatible solvent comprises an aqueous ethanol mixture having less than 20% (v/v) ethanol and from 0–1% (w/v) non-ionic detergent.

10. The method of claim 9 wherein the solvent further comprises physiologically compatible salts.

11. The method of claim 9 wherein the solvent comprises physiological saline and a maximum of 10% (v/v) ethanol.

12. The method of claim 9 wherein the solvent further comprises buffer salts at a pH within the normal pH range of human urine.

13. The method of claim 9 wherein the composition consists essentially of 0.05 $\mu$M-2 $\mu$M resiniferatoxin, 10% (v/v) ethanol and normal saline.

* * * * *